(12) United States Patent
Ubaldo et al.

(10) Patent No.: US 8,063,656 B1
(45) Date of Patent: Nov. 22, 2011

(54) METHOD OF ENABLING A CIRCUIT BOARD ANALYSIS

(75) Inventors: Pedro R. Ubaldo, Milpitas, CA (US); Leilei Zhang, Sunnyvale, CA (US)

(73) Assignee: Xilinx, Inc., San Jose, CA (US)

(*) Notice: Subject to any disclaimer, the term of this patent is extended or adjusted under 35 U.S.C. 154(b) by 345 days.

(21) Appl. No.: 12/403,563

(22) Filed: Mar. 13, 2009

(51) Int. Cl.
*G01R 31/28* (2006.01)

(52) U.S. Cl. ......... 324/763.01; 324/759.02; 324/763.02; 324/762.01; 324/762.02; 324/762.03; 324/757.02; 438/14; 438/15; 438/16; 438/17; 438/18

(58) Field of Classification Search .............. 438/14–18; 324/759.02, 763.01, 763.02, 762.01, 762.02, 324/762.03, 757, 2
See application file for complete search history.

(56) References Cited

U.S. PATENT DOCUMENTS

| | | | | |
|---|---|---|---|---|
| 5,424,652 A | * | 6/1995 | Hembree et al. | 324/756.02 |
| 5,698,474 A | * | 12/1997 | Hurley | 438/15 |
| 5,854,558 A | * | 12/1998 | Motooka et al. | 324/756.07 |
| 5,904,489 A | * | 5/1999 | Khosropour et al. | 438/15 |
| 6,020,748 A | * | 2/2000 | Jeng | 324/762.02 |
| 6,040,702 A | * | 3/2000 | Hembree et al. | 324/756.05 |
| 6,255,124 B1 | * | 7/2001 | Birdsley | 438/14 |
| 6,329,212 B1 | * | 12/2001 | Dobrovolski | 438/15 |
| 6,340,838 B1 | * | 1/2002 | Chung et al. | 257/668 |
| 6,590,409 B1 | * | 7/2003 | Hsiung et al. | 324/754.22 |
| 6,621,289 B1 | * | 9/2003 | Voogel | 324/762.03 |
| 7,112,983 B2 | * | 9/2006 | McGinnis et al. | 324/750.19 |
| 7,279,343 B1 | * | 10/2007 | Weaver et al. | 438/4 |
| 2003/0151421 A1 | * | 8/2003 | Leedy | 324/760 |
| 2004/0160240 A1 | * | 8/2004 | Ishida et al. | 324/765 |
| 2005/0136563 A1 | * | 6/2005 | Rowe et al. | 438/15 |
| 2006/0145720 A1 | * | 7/2006 | Zhang et al. | 324/763 |

* cited by examiner

*Primary Examiner* — Jermele M Hollington
*Assistant Examiner* — Lamarr Brown
(74) *Attorney, Agent, or Firm* — John J. King

(57) ABSTRACT

A method of enabling a circuit board analysis is disclosed. The method comprising removing a portion of the circuit board on a first side of the circuit board opposite a second side of the circuit board having an integrated circuit package; removing the circuit board from the integrated circuit package; performing a dye mapping to analyze bonds between the integrated circuit package and the circuit board; and performing an analysis of the integrated circuit package.

20 Claims, 3 Drawing Sheets

METHOD OF ENABLING A CIRCUIT BOARD ANALYSIS

FIELD OF THE INVENTION

The present invention relates generally to electronic circuits, and in particular, to a method of enabling a circuit board analysis.

BACKGROUND OF THE INVENTION

Failure analysis is an important part of the development of electronic devices, including circuit boards having integrated circuit packages. When assembling a circuit board, such as a printed circuit board, various stresses may lead to defects in solder connections between integrated circuit packages and contacts of the circuit board. There may also be stresses on the integrated circuit packages themselves. That is, there are a number of bonds within the integrated circuit packages which may be affected when the circuit board is assembled. For the circuit board to operate properly, components including integrated circuit packages must not only be properly attached to the circuit board, but must also be functioning.

When assembling a large volume of circuit boards, it is important to identify any processes which may cause defects in the circuit board or components of the circuit board. That is, in order to prevent any failure in the field, it is beneficial to identify failures before circuit boards are released, and identify the cause of the failures so that they may be eliminated. Further, it is beneficial to evaluate all elements of a given circuit board, including both the circuit board itself and components on the circuit board, to understand the impact of various processing steps and identifying solutions to improve the quality of circuit boards. However, when testing a circuit board, certain operations in the testing may impact components of the circuit board, limiting the ability to evaluate how processes for assembling and testing a circuit board may affect the various components of the circuit board.

SUMMARY OF THE INVENTION

A method of enabling a circuit board analysis is disclosed. The method comprising removing a portion of the circuit board on a first side of the circuit board opposite a second side of the circuit board having an integrated circuit package; removing the circuit board from the integrated circuit package; performing a dye mapping to analyze bonds between the integrated circuit package and the circuit board; and performing an analysis of the integrated circuit package. Removing a portion of the circuit board may comprise reducing the thickness of the circuit board so that the circuit board is weaker than the substrate of the integrated circuit package. The method may further comprise removing a lid of the integrated circuit package before removing the circuit board from the integrated circuit package and performing an analysis of the die of the integrated circuit package. Performing an analysis of the die of the integrated circuit package includes determining whether there is any delamination of the solder bumps between the die and the substrate of the integrated circuit package. Removing a portion of the circuit board on a first side of the circuit board includes performing a step of milling the first side of the circuit board. Performing an analysis of the integrated circuit package comprises performing an analysis of the silicon die of the integrated circuit package and performing substrate failure analysis for a substrate of the integrated circuit package.

According to an alternate embodiment, a method of enabling a circuit board analysis comprises applying a dye to solder bonds between an integrated circuit package and a circuit board; removing a portion of the circuit board on a first side of the circuit board opposite a second side of the circuit board having the integrated circuit package; peeling away the circuit board from the integrated circuit package; analyzing the solder bonds between the integrated circuit package and the circuit board based upon the location of the dye; and performing an analysis of the die of the integrated circuit package. Performing an analysis of the die of the integrated circuit package comprises analyzing the bonds between the die and the substrate of the integrated circuit package. The method may further comprise analyzing the substrate of the integrated circuit package. In addition, the method may further comprise applying a protective coating to the die before peeling away the circuit board from the integrated circuit package. The method may further comprise determining whether there is delamination in the bonds between the die and the substrate of the integrated circuit package, wherein the circuit board is removed by prying rather than removing a portion of the circuit board and peeling away the circuit board from the integrated circuit package. Removing a portion of the circuit board on a first side of the circuit board comprises reducing the thickness of the circuit board to less than the thickness of the substrate of the integrated circuit package. The method may further comprise generating a report related to the solder bonds and the integrated circuit package.

Further, a method of enabling a circuit board analysis may comprise removing a lid of an integrated circuit package coupled to the circuit board; analyzing a die of the integrated circuit package; removing a portion of the circuit board on a first side of the circuit board opposite a second side of the circuit board having an integrated circuit package; removing the circuit board from the integrated circuit package; analyzing solder bonds between the integrated circuit package and the circuit board; analyzing the die of the integrated circuit package after the circuit board is removed from the integrated circuit package; and generating a report for the solder bonds and the die of the integrated circuit package. The method may further comprise determining a high resistance area of the circuit board and cutting the high resistance area from the circuit board. Analyzing solder bonds between the integrated circuit package and the circuit board comprises analyzing ball grid array solder balls between the integrated circuit package and the circuit board. The method further comprises performing a dye and cure process before removing the lid, where analyzing the solder bonds comprises performing a die mapping. In addition, the method further comprises determining whether there is delamination in the bonds between the die and the substrate of the integrated circuit package, where the circuit board is removed by prying rather than removing a portion of the circuit board and removing the circuit board from the integrated circuit package if there is delamination. Performing an analysis of the die of the integrated circuit package comprises performing an analysis of the solder bumps between the die and the substrate.

DETAILED DESCRIPTION OF THE DRAWINGS

Figure 1:
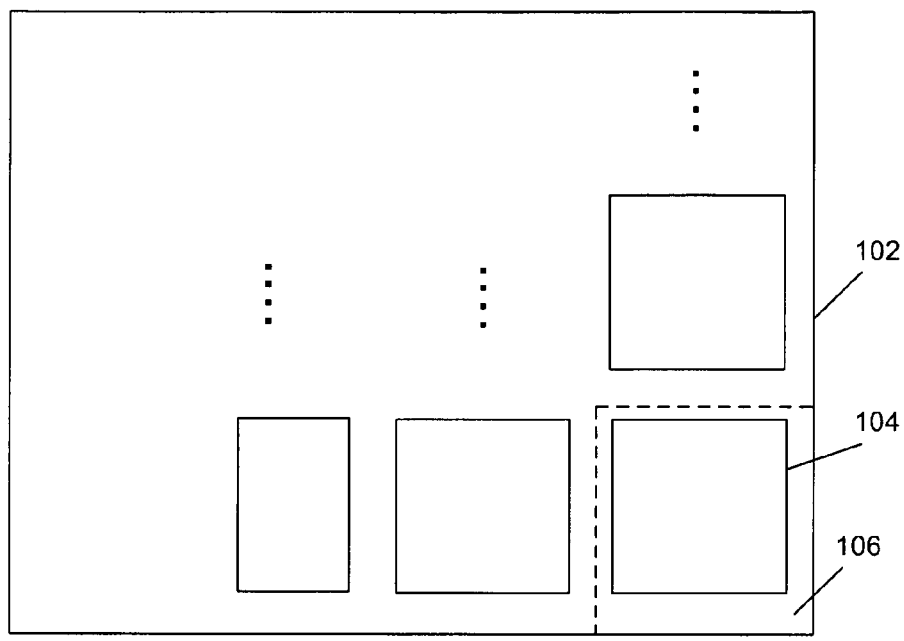
FIG. 1 is a block diagram of a circuit board having a plurality of integrated circuit devices according to an embodiment of the present invention.

Turning first to FIG. 1, a block diagram of a circuit board having a plurality of integrated circuit devices according to an embodiment of the present invention is shown. In particular, a circuit board 102 comprises a plurality of components mounted on the circuit board 102, including integrated circuit devices. As will be described in more detail below, an integrated circuit package 104 is coupled to the circuit board 102 by a plurality of solder bonds between contacts on the integrated circuit package and contact pads on the circuit board. As shown in the cross-sectional view of a portion 106 of the circuit board and integrated circuit package, the circuit board 102 has a thickness of $T_1$ and is coupled to receive the integrated circuit package 104. The circuit board may comprise any type of laminate material comprising alternating metal layers and conductive traces, as will be described in more detail below. The thickness of a circuit board is typically at least 93 mils (or approximately 2.36 millimeters (mm)).

The integrated circuit package comprises a substrate 202 having a thickness $T_2$, where the thickness $T_2$ may be approximately 1-2 mm. A die 204, such as a silicon die, is coupled to the substrate of the integrated circuit package by solder bumps 206 and corresponding contact pads 208 on a top surface of the substrate. Contact pads on the top surface of the substrate may be connected to contact pads 210 on the bottom surface of the substrate by circuit traces 212 provided for that purpose. The circuit traces may comprise conductors on a plurality of layers separated by dielectric layers. The circuit traces may be connected by vias between the various layers. A lid, such as a conductive lid functioning as a heat sink, is attached to the substrate to encapsulate the integrated circuit die. The lid may comprise foot portions 216 which are attached to the substrate by an adhesive 218. Another adhesive 220, such as a heat conducting adhesive, enables the lid to be attached to the die to provide further adhesive strength for the lid and improved thermal performance of the integrated circuit package. An underfill 222 may be provided between die and the substrate. Solder balls 224 are coupled to the contact pads 210 on the bottom of the substrate are provided to enable a connection to contact pads 226 on the circuit board. Conductors 228 of the circuit board enable connections between contacts of a component on the circuit board, between components on the circuit board, and between a component on the circuit board and a connector for the circuit board.

Figure 2:
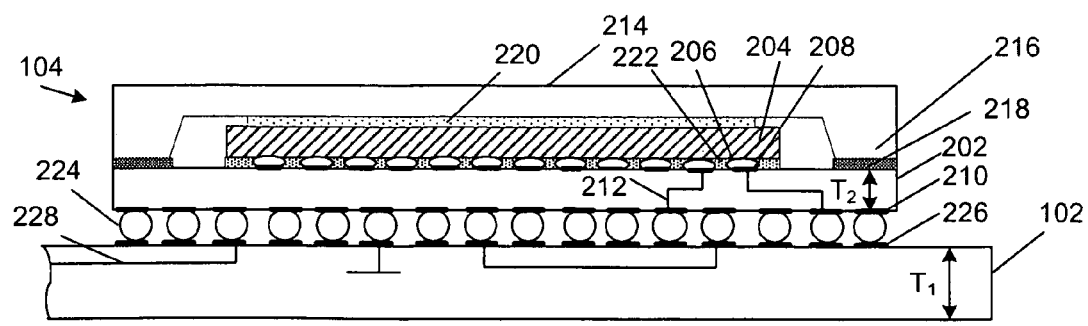
FIG. 2 is a cross-sectional view of a portion of the circuit board and an integrated circuit package according to an embodiment of the present invention.
Figure 3:
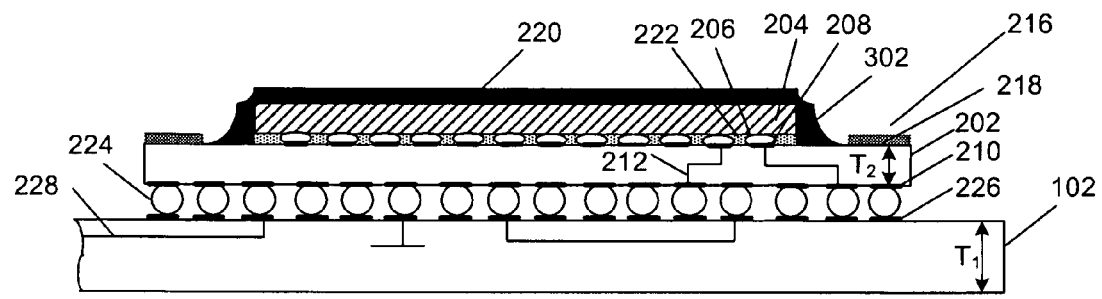
FIG. 3 is a cross-sectional view of the portion of the circuit board and integrated circuit package of FIG. 2 with the lid of the integrated circuit package removed according to an embodiment of the present invention.

Turning now to FIG. 3, a cross-sectional view of the portion of the circuit board and integrated circuit package of FIG. 2 with the lid 214 of the integrated circuit package removed according to an embodiment of the present invention is shown. In particular, lid 214 is removed to enable analysis of the die. For example, a scan of the device may be performed using C-Code Scanning Acoustic Microscopy (CSAM). CSAM enables analysis of surface materials such as pores and cracks as is well known in the art. However, other or additional processes for detecting defects in the die or in connections between the die and the substrate may be performed. A protective coating 302, such as an epoxy or resin, may then be applied to die to encapsulate the die and protect the die and solder bumps for further analysis after the circuit board is removed from the integrated circuit package.

Figure 4:
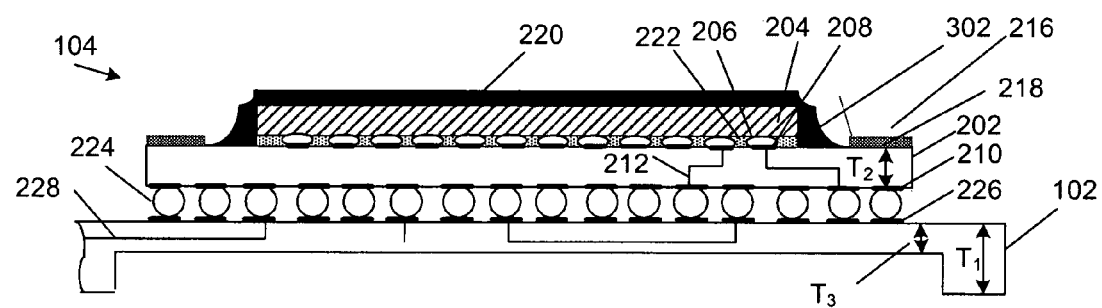
FIG. 4 is a cross-sectional view of the portion of the circuit board and the integrated circuit package of FIG. 3 after milling according to an embodiment of the present invention.

Turning now to FIG. 4, a cross-sectional view of the portion of the circuit board and the integrated circuit package of FIG. 3 after a portion of the circuit board is removed according to an embodiment of the present invention is shown. In particular, the bottom portion of the circuit board is milled such that the thickness of the circuit board is reduced to a thickness $T_3$. The thickness $T_3$ is selected such that the strength of the substrate of the integrated circuit package is greater than the strength of the circuit board at the location of the integrated circuit package after the thickness of the circuit board is reduced. The reduction in thickness of the circuit board may be performed by any type of thinning technique, including grinding, milling, etching, etc. According to one embodiment, the thickness of the circuit board is reduced to a thickness which is less than the thickness of the substrate. It should be noted that the underfill may make the substrate somewhat stronger, and therefore may affect the thickness $T_3$ to which the circuit board must be reduced. While the substrate and the circuit board material may generally have about the same strength, the additional strength provided by the underfill may enable the circuit board to be reduced to a thickness which is greater than the substrate while still enabling the circuit board to be peeled away from the integrated circuit package without damaging the die. Although only a portion of the circuit board below the integrated circuit package is shown having a reduced thickness, the entire section 106 of the circuit board or the entire board may be processed to have a reduced thickness.

Figure 5:
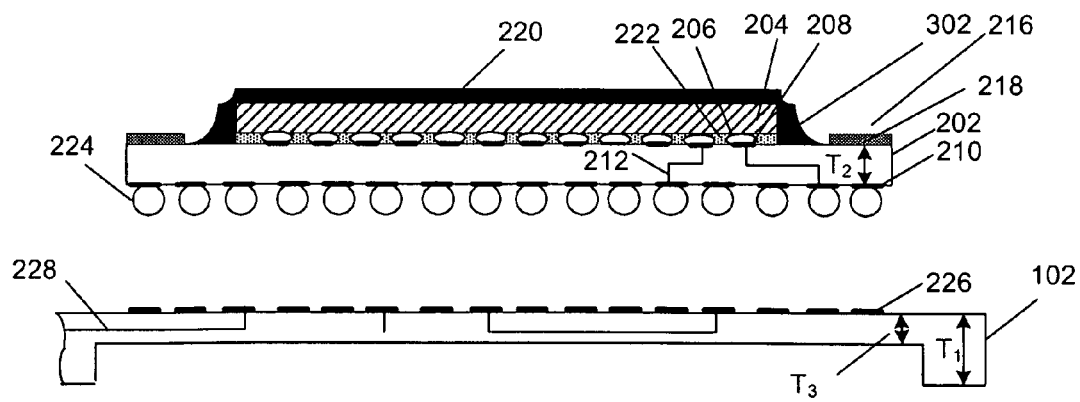
FIG. 5 is a cross-sectional view of the portion of the circuit board and the integrated circuit package of FIG. 4 according to an embodiment of the present invention.

As shown in the embodiment of FIG. 5, a cross-sectional view of the portion of the circuit board and the integrated circuit package of FIG. 4 after the circuit board is removed from the integrated circuit package is shown. In particular, the circuit board is removed from the integrated circuit package by a peeling action. Because the strength of the substrate is greater than the strength of the circuit board after the thinning process, the substrate and the die remain in tack as the circuit board is pulled away from integrated circuit package. That is, reducing the thickness of the circuit board enables analysis of both the solder bonds between the integrated circuit package and the circuit board and the integrated circuit package itself. Because neither the die nor the substrate will be cracked after the circuit board is removed from the integrated circuit package, the die and substrate may be analyzed for any damage or failures which may result from the assembly or testing processes.

Figure 6:
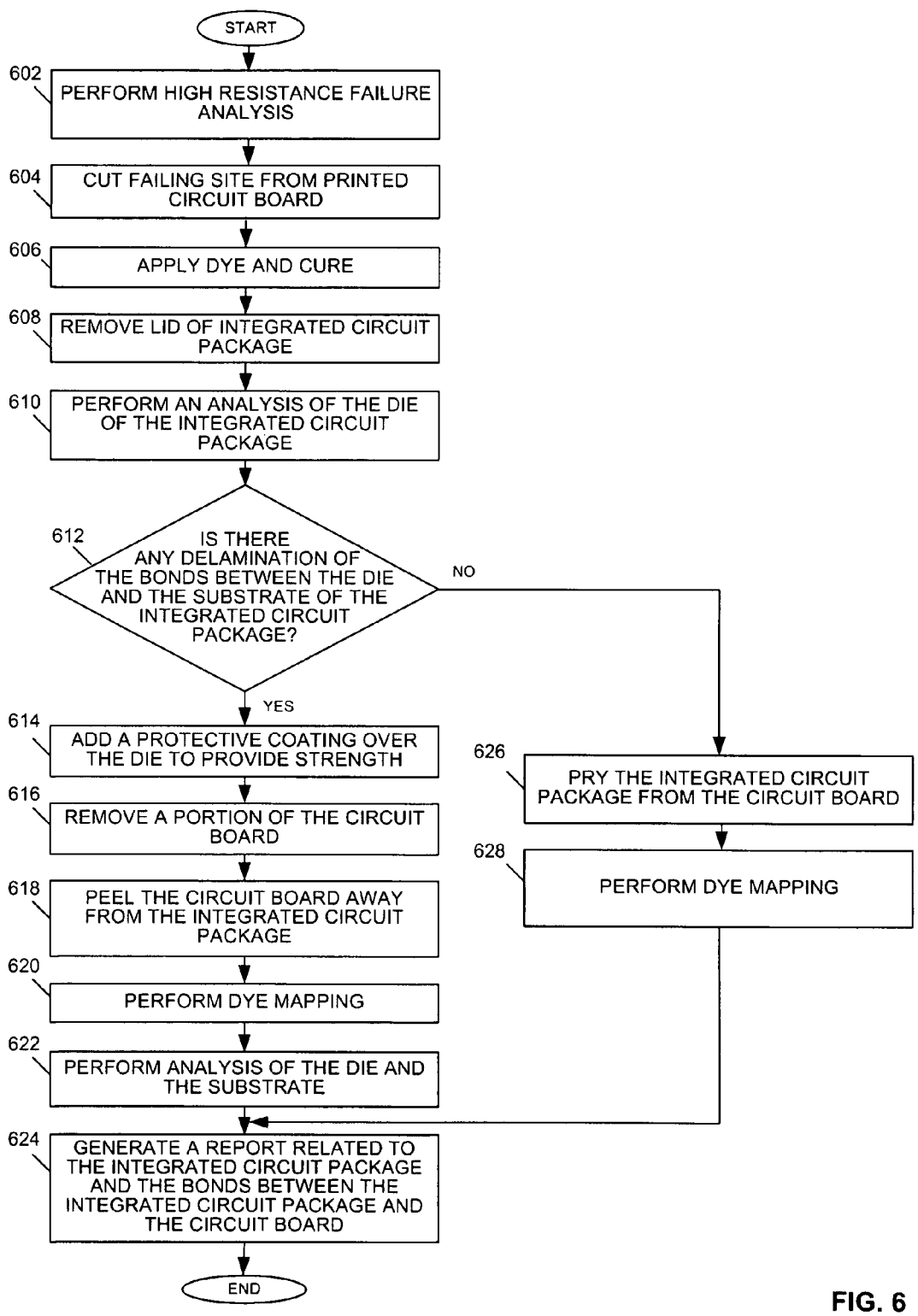
FIG. 6 is a flow chart showing a method of enabling circuit board analysis according to an embodiment of the present invention.

Turning now to FIG. 6, a flow chart shows a method of enabling circuit board analysis according to an embodiment of the present invention. In particular, a high resistance failure analysis is performed at a step 602. For example, probes may be applied to leads, solder bumps or contact pads associated with the integrated circuit package. A high resistance failure may be detected after a voltage is applied to a certain lead, solder bump or contact pad and a signal is not detected at another lead, solder bump or contact pad as would be expected. A failing site may then be cut from circuit board at a step 604. Cutting the failing site from the circuit board may make it easier to reduce the thickness of the circuit board near the integrated circuit package. A dye is applied and cured at a step 606. The dye is used to detect solder ball or contact pad cracking. The lid of integrated circuit package is removed at a step 608, and an analysis of the die of the integrated circuit package is performed at a step 610. For example, the integrated circuit package may be inspected for any cracks in the solder mask, and a scan of the device may be performed CSAM to identify any defects in the solder bumps between the die and the substrate of the integrated circuit package. It is then determined if there is any delamination of the bonds between the die and the substrate of the integrated circuit package at a step 612. That is, it is determined if there is any failure in the solder bumps between the die and the substrate. If there is delamination, a coating may then be added over the die at a step 614 to strengthen the die for the remaining steps of the processes. For example, an epoxy or resin material may then be applied over the die to encapsulate the die, protecting the die when the circuit board is thinned and peeled away from the integrated circuit package.

A portion of the circuit board is then removed at a step 616 by a thinning technique such as milling as described above. The circuit board is then peeled away from the integrated circuit package at a step 618. A dye mapping is performed at a step 620 to identify locations of cracking in any of the solder bonds. Analysis of the die and the substrate is performed at a step 622. Because the die and the substrate are not damaged during the thinning and peeling steps, the die and substrate may be analyzed for any defects or damage which may be present, including any damage resulting from the assembly or testing of the circuit board. A pot sample of the die may be taken, where a cross section of the die and substrate is taken, allowing analysis of the solder bumps between the die and the substrate. A report related to the integrated circuit package and the bonds between the integrated circuit package and the circuit board is generated at a step 624. In certain circumstances where there is no delamination between the die and the substrate, such as circumstances when it may be determined that there is no damage to the die and it would not be possible to perform the desired tests to the die, the thinning process may be skipped. In that case, the integrated circuit package is pried from the circuit board at a step 626 and a dye mapping is performed at a step 628.

It can therefore be appreciated that the new and novel method of enabling a circuit board analysis has been described. It will be appreciated by those skilled in the art that numerous alternatives and equivalents will be seen to exist which incorporate the disclosed invention. As a result, the invention is not to be limited by the foregoing embodiments, but only by the following claims.

We claim:

1. A method of enabling a circuit board analysis, the method comprising:
    removing a portion of the circuit board on a first side of the circuit board opposite a second side of the circuit board having an integrated circuit package;
    removing the circuit board from the integrated circuit package;
    performing a dye mapping to analyze bonds between the integrated circuit package and the circuit board; and
    performing an analysis of the integrated circuit package.

2. The method of claim 1 wherein removing a portion of the circuit board comprises reducing the thickness of the circuit board so that the circuit board is weaker than the substrate of the integrated circuit package.

3. The method of claim 1 further comprising removing a lid of the integrated circuit package before removing the circuit board from the integrated circuit package and performing an analysis of the die of the integrated circuit package.

4. The method of claim 3 wherein performing an analysis of the die of the integrated circuit package comprises determining whether there is any delamination of the solder bumps between the die and the substrate of the integrated circuit package.

5. The method of claim 1 wherein removing a portion of the circuit board on a first side of the circuit board comprises milling the first side of the circuit board.

6. The method of claim 1 wherein performing an analysis of the integrated circuit package comprises performing an analysis of the silicon die of the integrated circuit package.

7. The method of claim 1 wherein performing an analysis of the integrated circuit package comprises performing substrate failure analysis for a substrate of the integrated circuit package.

8. A method of enabling a circuit board analysis, the method comprising:
    applying a dye to solder bonds between an integrated circuit package and a circuit board;
    removing a portion of the circuit board on a first side of the circuit board opposite a second side of the circuit board having the integrated circuit package;
    peeling away the circuit board from the integrated circuit package;
    analyzing the solder bonds between the integrated circuit package and the circuit board based upon the location of the dye; and
    performing an analysis of the die of the integrated circuit package.

9. The method of claim 8 wherein performing an analysis of the die of the integrated circuit package comprises analyzing the bonds between the die and the substrate of the integrated circuit package.

10. The method of claim 8 further comprising analyzing the substrate of the integrated circuit package.

11. The method of claim 8 further comprising applying a protective coating to the die before peeling away the circuit board from the integrated circuit package.

12. The method of claim 8 further comprising determining whether there is delamination in the bonds between the die and the substrate of the integrated circuit package, wherein the circuit board is removed by prying rather than removing a portion of the circuit board and peeling away the circuit board from the integrated circuit package if there is delamination.

13. The method of claim 8 wherein removing a portion of the circuit board on a first side of the circuit board comprises reducing the thickness of the circuit board to less than the thickness of the substrate of the integrated circuit package.

14. The method of claim 8 further comprising generating a report related to the solder bonds and the integrated circuit package.

15. A method of enabling a circuit board analysis, the method comprising:
    removing a lid of an integrated circuit package coupled to the circuit board;
    analyzing a die of the integrated circuit package;
    removing a portion of the circuit board on a first side of the circuit board opposite a second side of the circuit board having an integrated circuit package;
    removing the circuit board from the integrated circuit package;
    analyzing solder bonds between the integrated circuit package and the circuit board;
    analyzing the die of the integrated circuit package after the circuit board is removed from the integrated circuit package; and generating a report for the solder bonds and the die of the integrated circuit package.

16. The method of claim 15 further comprising determining a high resistance area of the circuit board and cutting the high resistance area from the circuit board.

17. The method of claim 16 wherein analyzing solder bonds between the integrated circuit package and the circuit board comprises analyzing ball grid array solder balls between the integrated circuit package and the circuit board.

18. The method of claim 15 further comprising performing a dye and cure process before removing the lid, wherein analyzing solder bonds comprises performing a die mapping.

19. The method of claim 15 further comprising determining whether there is delamination in the bonds between the die and the substrate of the integrated circuit package, wherein the circuit board is removed by prying rather than removing a portion of the circuit board and removing the circuit board from the integrated circuit package if there is delamination.

20. The method of claim 15 wherein performing an analysis of the die of the integrated circuit package comprises performing an analysis of the solder bumps between the die and the substrate.

* * * * *